United States Patent [19]

Cannon, III

[11] 4,108,148

[45] Aug. 22, 1978

[54] PACER WITH AUTOMATICALLY VARIABLE A-V INTERVAL

[75] Inventor: Robert Lee Cannon, III, Waltham, Mass.

[73] Assignee: Sheldon Thaler, Princeton, N.J.

[21] Appl. No.: 738,418

[22] Filed: Nov. 3, 1976

[51] Int. Cl.$^2$ ............................................. A61W 1/36
[52] U.S. Cl. ............................................ 128/419 PG
[58] Field of Search ............ 128/419 PG, 419 R, 421, 128/422, 423

[56] References Cited

U.S. PATENT DOCUMENTS

| 3,253,596 | 5/1966 | Keller, Jr. | 128/419 PG |
|---|---|---|---|
| 3,433,228 | 3/1969 | Keller, Jr. | 128/419 PG |
| 3,648,707 | 3/1972 | Greatbatch | 128/419 PG |
| 3,783,878 | 1/1974 | Thaler et al. | 128/419 PG |
| 3,794,045 | 2/1974 | Thaler | 128/418 PG |
| 3,807,410 | 4/1974 | Wall et al. | 128/419 PG |
| 3,903,897 | 9/1975 | Woollows et al. | 128/419 PG |

OTHER PUBLICATIONS

Fischler et al. "IEEE Transactions on Biomedical Engineering vol. BME 16, #1, Jan., 1969, pp. 64–68.

*Primary Examiner*—William E. Kamm

*Attorney, Agent, or Firm*—Jeremiah J. Duggan; Stephen A. Schneeberger

[57] ABSTRACT

An improved atrial synchronous heart pacer includes means for generating an atrio-ventricular (A-V) interval control signal of automatically variable duration, which duration is a function of the sensed atrial heart rate (i.e. P-wave rate). A timing circuit establishes a basic timing interval for the generation of ventricular stimulation pulses, which interval may be modified by the control of the A-V interval signal. The A-V interval control signal preferably comprises the output of a P-wave triggered monostable multivibrator. The time constants of the multivibrator's timing circuits are scaled such that operation within the heart-rate range of 55-150 beats per minute prevents full recovery of the multivibrator following each sensed atrial beat and generation of an A-V output pulse, resulting in an A-V output pulse whose duration is a function of the time since the preceding trigger (i.e. rate).

By appropriately coupling the variable duration A-V interval pulse to the ventricular stimulation pulse timing circuitry, it is possible to adjust the threshold voltage of a relaxation oscillator such that the ventricular stimulation pulse is generated at the end of an A-V delay following a sensed P-wave, the interval of the A-V delay being variable and dependent on the P-wave rate.

7 Claims, 8 Drawing Figures

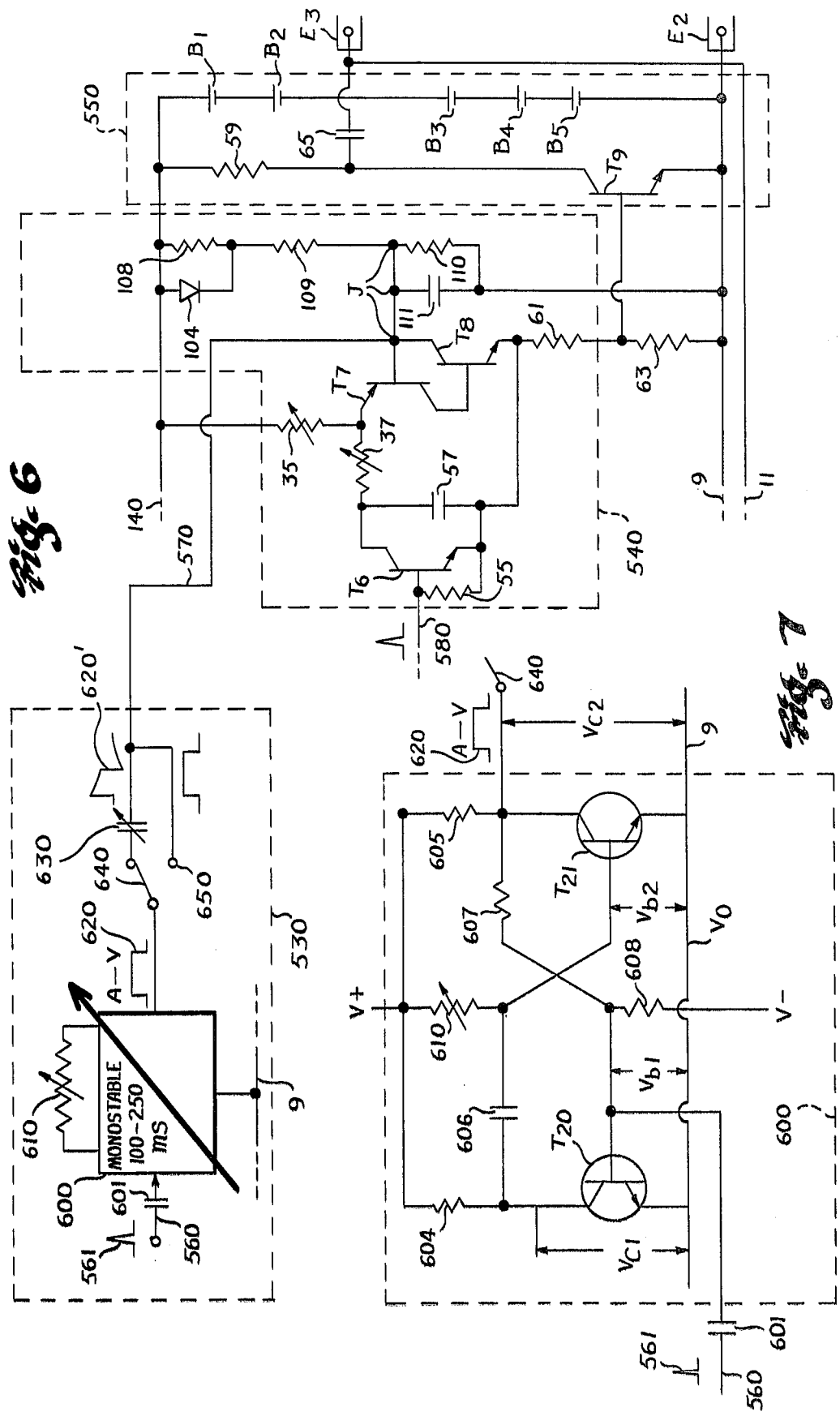

PACER WITH AUTOMATICALLY VARIABLE A-V INTERVAL

BACKGROUND OF THE INVENTION (1) Field of the Invention

The present invention relates generally to heartstimulation devices, and particularly to atrial synchronous heart stimulation devices.

(2) Description of the Prior Art

In the field of medical electronics, heart pacers are becoming widely accepted and well known at this juncture. There are several varieties of heart pacer available on the market today. There are pacers which provide stimulation to the ventricle of the heart at a fixed rate, pacers which provide stimulation to the ventricle of the heart on demand, pacers which provide stimulation to the atrium and ventricle of the heart in a predetermined timing sequence and on demand, and pacers which provide stimulation to the ventricle in response to signal inputs received from the patient's body other than from the ventricular chambers of the patient's heart. (By no means is this listing intended to include all types of pacers available today.) It is with this last mentioned type of heart pacer that the present invention is more particularly related.

In a normally functioning heart, the sinoatrial mode initiates depolarization of the elctrically polarized muscalature of the heart and serves as the normal pacemaker of the heart. The depolarization initially causes contraction of the atria, as represented by the electrical P-wave, and subsequently causes contraction of the ventricles (represented by the QRS complex) following a delay known as the A-V delay. The A-V mode is responsible for the A-V delay which ensures proper asynchronous contraction of the atria and ventricles for efficient cardiac hemodynamics. In fact, the A-V delay comprises by far the major portion of the P-R delay which also includes the time required to excite the atria and the time occupied by conduction from the A-V mode to the ventricular myocardium. However, the A-V delay is not constant at all heart rates. Instead, it varies from a relatively long interval (i.e. 170-250 milliseconds) for slow heart rates (i.e. 55-70 beats per minute) to a relatively short interval (i.e. 125-170 milliseconds) for rapid heart rates (i.e. 130-150 beats per minute), with the A-V delay in the adult human heart tending to be greater than that in a child's heart at any particular heart rate. The pacer of the invention is particularly suited for use when so-called A-V block prevents normal conduction of the depolarizing voltage from the atria to the ventricles.

Detected P-waves representing atrial contractions of the heart have been used to control the timing of ventricular stimulation pulses. Such pacers may be generally designated as being atrial synchronous. The U.S. Pat. No. 3,648,707 which issued on Mar. 14, 1972 is cited as a somewhat limited example of this prior art. That patent describes a device which can detect P-waves and which causes a ventricular pulse generator to supply a stimulation pulse at a fixed interval (A-V interval) of time after the P-wave detection occurred. If no P-wave occurs, the pacer provides a stimulation to the ventricle of the heart at the end of a predetermined interval from the previous ventricular heart beat or stimulation. If a P-wave is sensed at or near the time of occurrence of the ventricular stimulation impulse, the ventricular stimulation impulse still occurs at the expected time, This results in an upper limit on the interval between the ventricular stimulation impulses, or in other words, a lower limit to rate.

More recently, there has been developed a heart pacer which responds to sensed P-waves and includes timing and control means for generating a fixed-interval A-V interval pulse which (unless inhibited by a natural ventricular contraction) acts, at its conclusion, to generate a ventricular stimulation impulse even if the P-wave occurs only shortly before the expiration of the predetermined basic timing interval initiated by the previous ventricular beat or stimulation. This latter pacer is designed such that the basic timing interval provides a practical intermediate or median stimulation rate, which stimulation rate may decrease for relaxation or sleep, and alternatively increase for exercise, as a function of the rate of atrial contractions.

Even though the pacer described immediated above represents a significant advance in heart pacers by its ability to vary the ventricular stimulation rate as a function of the atrial beating rate, it may not exactly stimulate the heart's conduction system because it relies on an A-V interval of fixed duration independent of heart rate. The use of a constant A-V interval may also tend to limit the practical range of heart rates over which the atrial synchronous pacer is operable.

It is, therefore, a principal object of the invention to provide an improved pacer responsive to a sensed P-wave for generating a ventricular stimulation pulse following an A-V delay interval of automatically determined length or duration. Included within this object is the provision of means for automatically determining the interval of the A-V delay as a function of the atrial beating rate.

It is another object of the invention to provide an improved heart pacer which is responsive to atrial contractions and accurately stimulates or approximates the natural conduction system of the heart.

SUMMARY OF THE INVENTION

In accordance with the invention there is provided an improved atrial synchronous heart-stimulating device or pacer having terminal means for connection to a patient's heart, timing circuitry for establishing timing intervals based on a basic interval, pulse generating circuitry for generating a ventricular stimulation impulse on the terminal means at the end of each of the timing intervals to effect a beating action of the ventricle of the heart, a P-wave detector or the like for detecting the beating action of the heart's atrium, circuitry responsive to the P-wave detector for generating an atrialventricular (A-V) interval pulse, the timing circuitry including control circuitry responsive to the A-V interval pulse for varying the timing interval relative to the basic interval within a predetermined range, the completion of the varied timing interval coinciding with the completion of a respective A-V interval pulse, and circuitry responsive to at least the ventricular stimulation impulse for resetting the timing means and wherein the improvement comprises the A-V interval pulse generating circuitry comprising circuitry responsive to successively detected beating actions of the atrium of the heart for automatically controlling the interval of the respectively generated A-V interval pulse as a function of the interval between the successively detected atrial beating actions. The circuitry for resetting the timing means is preferably responsive to the beating action of the heart's ventricle, which occurs either naturally (demand operation) or in response to the ventricular stimulation impulse.

The A-V interval pulse generating circuitry is responsive to variations in the interval between successive atrial beating actions to vary the interval of the respective A-V interval pulse in the same time-sense direction.

In a preferred embodiment, the A-V interval pulse generating means comprises a monostable multivibrator having first RC timing circuitry for determining the normal maximum duration of the A-V interval pulse and second RC timing circuitry for determining the minimum time for full recovery between successive A-V interval pulses of the normal maximum duration, the monostable being triggered by each detected atrial beating action. The A-V interval pulse is of less than the maximum duration if the respective triggering of the monostable occurs sooner than completion of the full recovery following termination of the preceding A-V interval pulse and the first and second RC timing circuits are preselected to provide an A-V interval pulse of first duration when the interval between successive atrial beating actions is of one value and of second duration shorter than the first duration when the interval between successive atrial beating actions is of another value-shorter than the first value. The one interval between successive atrial beats may correspond with a low-limit heart rate (e.g. 55–60 b.p.m.) and the other may correspond with a high-limit heart rate (e.g. 140–150 b.p.m.). The variation in the interval of the A-V interval pulse is substantially continuous across the heart rate range between the high and low limits.

The control circuitry for varying the pacer's timing interval from the basic interval comprises circuitry for lengthening the timing interval beyond the basic interval if the otherwise next generated one of the ventricular stimulation pulses would have occurred during the time of occurrence of the A-V interval pulse and for limiting the lengthened interval to be no longer than the sum of the basic interval and that of the A-V interval pulse and alternatively for shortening the timing interval to less than the basic interval if the detected beating action of the heart's atrium occurs within a predetermined interval which ends prior to the end of the basic interval by the length or interval of the A-V interval pulse.

DESCRIPTION OF THE DRAWING

FIG. 6 is a more detailed circuit diagram of portions of the pacer illustrated in FIG. 5.

FIG. 7 is a detailed schematic diagram of the monostable multivibrator comprising the interval control for providing A-V interval pulses in which the respective intervals are P-wave-rate-dependent.

DESCRIPTION OF THE PREFERRED EMBODIMENTS

Figure 1:
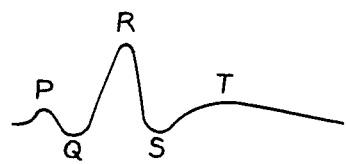
FIG. 1 illustrates the voltage wave produced by the heart during one complete heart beat.

The human heartbeat is represented electrically as a complex wave consisting of what are designated P,Q,R,S and T waves as shown in FIG. 1. The P-wave represents an atrial beat associated with atrial depolarization, which beat commands the heart rate as a function of signals from the rest of the body. The major and most pronounced electrical pulse in the heart is the R-wave. The R-wave, which represents ventricular contraction, typically has an amplitude relation to the P-wave of at least 3:1, although it will be appreciated that the P-wave may be of equal or greater magnitude than the R-wave if both are sensed in the atrium. The R-wave normally represents depolarization of the ventricles, but when not occurring due to some cardiac malfunction it is a function of the artificial pacer to provide periodic electronic pulses to the heart to stimulate contraction. If both the natural and artificial pacer supply an R-wave, however, competition for control of the heart results and a possibly dangerous situation arises when the pacer electronic pulse occurs in a T-wave region, or so called "vulnerable period". To avoid this problem, there has been developed a so-called demand pacer as typified in U.S. Pat. No. 3,528,428, the subject matter of which is incorporated herein by reference.

Figure 5:
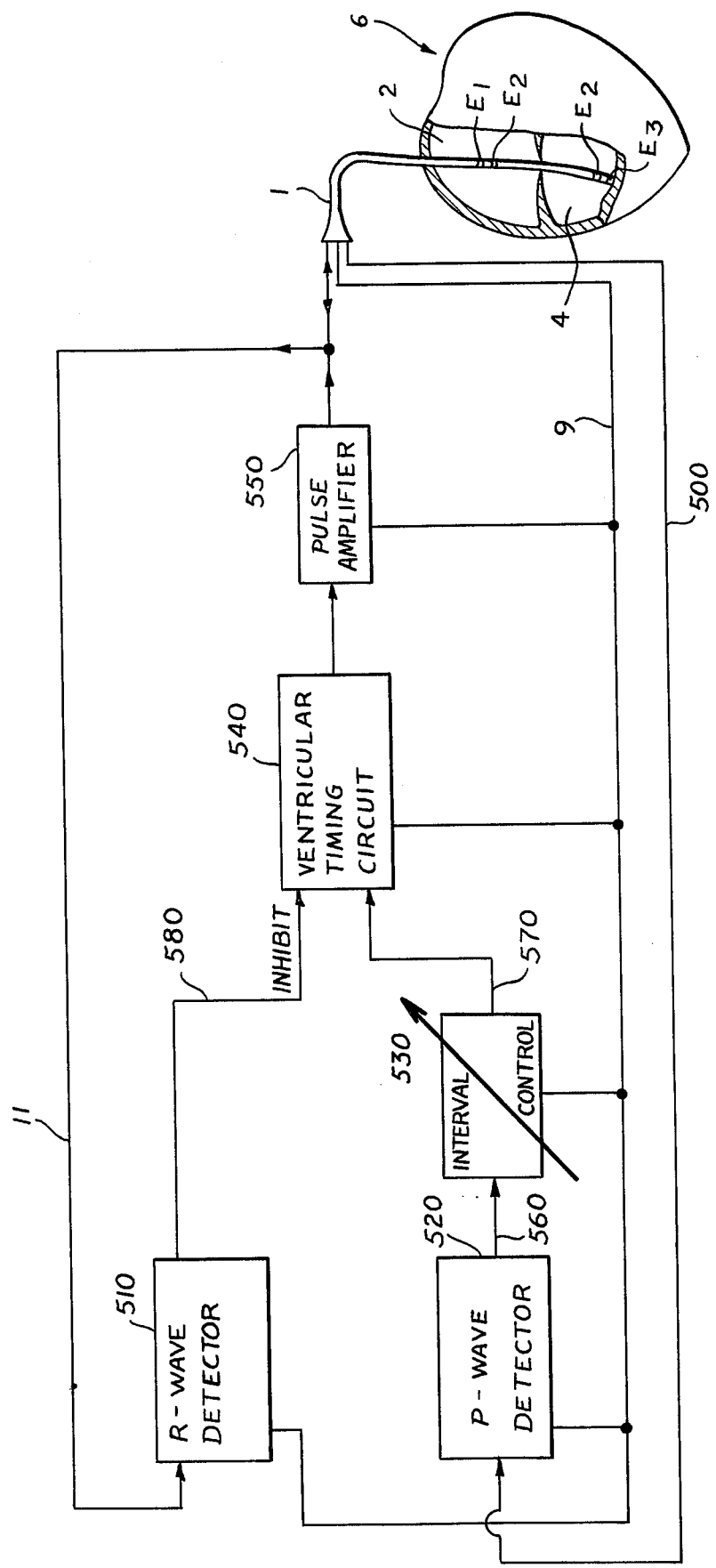
FIG. 5 is a block diagram illustrating a preferred embodiment of the pacer of the invention.

Referring to FIG. 5, there is illustrated in diagrammatic form an artificial pacer constructed in accordance with the invention and having a catheter 1 operatively connected thereto for positioning electrode pole E1 and E2' in the atrium 2 and electrode poles E2 and E3 in the ventricle 4 of heart 6. The catheter 1 is inserted into the heart 6 until its electrode pole tip E3 lodges in the apex of the ventricle. Electrode pole E2 in the ventricle 4 is closely spaced from electrode pole E3, and similarly electrode pole E2' in the atrium 2 is closely spaced from electrode pole E1. The spacing between electrode poles E1 and E3 is preferably about 11 centimeters such that pole E3 contacts the apex of ventricle 4 and electrode E1 is spaced relatively distantly therefrom in the atrium 2. This degree of spacing between electrodes E1 and E3 is preferred in order to maximize the sensing of the P-wave. Myocardial implantation of the electrodes will, of course, provide a suitable alternative, as will the use of separate transvenous electrodes.

Electrode pole E1 is connected through conductor 500 to the input of a P-wave detector 520 for conveying sensed P-waves thereto. Similarly, the ventricular QRS complex sensed by electrode pole E3 is conveyed by conductor 11 to the input of an R-wave detector 510. Conductor 11 additionally extends to the output of pulse amplifier 550 of the pacer from which it receives the ventricular stimulation pulses applied to ventricle 4 by means of electrode pole E2' and E3. Electrode poles E2 in the atrium 2 and the ventricle 4 respectively are connected electrically in common to conductor 9 to provide a common or "ground" electrical reference level connected to some respective portions of the pacer. The R-wave detector 510 and P-wave detector 520 are capable of providing pulses indicative of the detection of a QRS complex and a P-wave respectively. While it may be possible to use various types of P-wave and R-wave detectors, these detectors in the preferred embodiment are constructed in accordance with the teachings of the aforementioned U.S. Pat. No. 3,528,428. The present R-wave detector 510 is substantially identical to the QRS complex detection circuitry and rate discriminator stage of the aforementioned U.S. Pat. No. 3,528,428.

The P-wave detector 520 is essentially the same as the R-wave detector circuitry 510, each detector including band-pass filters, however the filters associated with the amplifying stages of P-wave detector 520 are scaled to have a somewhat higher pass-band center frequency than the filters of the R-wave detector (e.g. 80 Hz vs 40 Hz), to optimize their sensitivity and response to the P-wave and QRS complex respectively as discussed in U.S. Application Ser. No. 726,887 filed Sept. 27, 1976, by S. S. Thaler for P-Wave Control, R-Wave Inhibited Ventricular Stimulation Device which is incorporated herein by reference.

Figure 2:
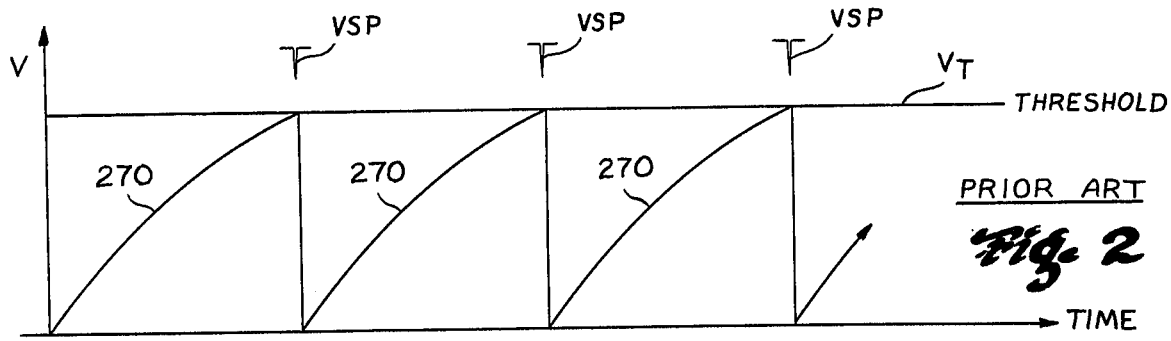
FIG. 2 comprises a sequential graphical representation of the voltage appearing across the timing capacitor of the pacer's relaxation oscillator relative to the threshold voltage for controlling the generation of stimulation pulses, as known in the prior art.

Ventricular timing circuit 540 is operative in a free running or continuously operating mode, known in the prior art, to provide pulses recurring at a regular or so-called "basic" interval, as illustrated by pulses VSP of FIG. 2, those pulses being amplified by pulse amplifier 550 and applied to electrode E3 through conductor 11 for stimulation of the ventricle 4. The ventricular timing circuit 540 is essentially comprised of a relaxation oscillator having a basic timing interval in the free running mode and which is inhibited by a rest pulse on conductor 580 from R-wave detector 510 each time an R-wave appears on conductor 11, as required for "demand" operation. The automatically variable interval controller 530 of the invention forms part of the general pacer timing circuitry through conductor 570 and is responsive to pulses appearing on conductor 560 from the output of P-wave detector 520 each time an atrial P-wave is detected for adjusting or controlling the timing of ventricular timing circuit 540.

Through the appropriate selection of components and their values in interval control circuit 530 and in conjunction with the circuitry of ventricular timing circuit 540, the pacer of the invention is capable of adjusting the timing of circuit 540 such that the ventricular stimulation impulses normally occur following an automatically variable delay or interval (termed the A-V interval) after the occurrence of a detected atrial P-wave. The interval between successive ventricular stimulation pulses may be increased and/or decreased relative to the regular or basic interval in accordance with a respective decrease and/or increase in the atrial P-wave rate.

Further, in accordance with the invention, the duration of the interval is automatically determined as a function of the heart rate as measured by the detected P-waves.

The basic timing interval of ventricular timing circuit 540 may be established as that providing a stimulation pulse rate of about 75 beats per minute, and the P-wave rate may then act to slow this rate as for relaxation or sleeping and additionally may act to accelerate the rate as during exercise. Even if the P-wave detection and interval controlling circuitry added by the invention is ineffective, as due to the absence of atrial P-waves or a failure in that processing circuitry, the pacer will continue to operate as a conventional demand pacer at a stimulation rate (75 beats per minute, 800 ms. intervals) which is clearly adequate for life support and well within the upper and lower limits.

Reference is now made to FIG. 6 which is a partially diagramatic schematic of the illustrative embodiment of the illustrative embodiment of the present invention. The schematic of FIG. 6 is to be viewed in conjunction with FIG. 1 of the aforementioned U.S. Pat. No. 3,528,428, the exact combination of which provides an operative embodiment except for the inclusion of P-wave detector 520. Accordingly, to the extent that U.S. Pat. No. 3,528,428 is incorporated for its disclosure of R-wave detector 510, it is similarly incorporated for the teaching of a detector such as P-wave detector 520 which differs from the R-wave detector 510 in only the relatively few ways mentioned. The following components of FIG. 6 of the instant application are identical to components of FIG. 1 of this patent: the transistors T6, T7, T8 and T9; resistors 35,37,55,61,63 and 59; capacitors 57 and 65; electrodes E1 and E2; and conductors 9 and 11. Interconnection of these components is described in this patent. Other components in FIG. 6 of the instant application may be equivalent to components in FIG. 1 of this patent, but are given different reference numerals.

In addition to that material disclosed in U.S. Pat. No. 3,528,428 which is incorporated herein by reference, certain other portions of the pacer as illustrated in FIG. 6 are described in U.S. Pat. No. 3,774,619 to which reference may be made for additional information. Specifically, batteries B1, B2, B3, B4 and B5, the parallel connected compensating diode 104 and resistor 108, the resistor 109 in series with resistor 108 and the parallel-connected capacitor 111 and resistor 110 in series with resistor 109. The junction of resistors 109 and 110 (junction J) is connected to the base of transistor T7 and the potential of this junction is the threshold level of the timing circuitry. Certain other elements of U.S. Pat. No. 3,774,619 have been omitted inasmuch as they do not affect the substance of the present invention.

In accordance with an aspect of the invention, the P-wave detector 520 and interval control 530 are operatively connected to junction J of the pacer timing circuitry to adjust the threshold potential level threat in response to the detection of atrial P-waves in heart 6. The interval control 530 as illustrated in FIG. 6 includes a monostable multivibrator or one-shot 600 designed according to the invention for generating an A-V interval pulse of predetermined, automatically variable duration in response to a trigger pulse received from the output of P-wave detector 520, as will be explained hereinafter in greater detail. A variable resistor 610 enables the monostable 600 to be preset to provide a nominal A-V delay pulse having an interval typically equal to or greater than 250 milliseconds.

The A-V interval pulse 620 at the output of monostable 600 is of rectangular waveform and may be one embodiment of the invention, connected substantially directly to junction J. In another embodiment of the invention A-V interval pulse 620 is extended to junction J through a capacitor 630 to obtain a preselected "droop" in the pulse waveform voltage applied to junction J. While these two embodiments might normally appear in separate pacers, in the interest of brevity they have been combined in FIG. 6 and illustrated as being available in a single pacer through use of a presettable single pole, double throw switch 640.

One pole of switch 640 is connected to the output of monostable 600 and the other pole is selectively connectable either to one end of capacitor 630 (as shown) or to terminal 650 of a bypass conductor connected to the conductor 570 and the other end of capacitor 630. Also for the purpose of illustrating the invention, the capacitor 630 is shown as being variable to illustrate that the extent of droop introduced to A-V delay pulse 620 may be varied as will be described.

Interrelating the circuitry of the instant application with U.S. Pat. No. 3,528,428, conductor 140 is connected to the junction to resistors 29, 31 and 33 in that patent. Conductor 580 is connected to the side of capacitor 53 remote from the side which is connected to the junction of capacitor 49 and resistors 47 and 45 in that patent. In this illustrative embodiment of the present invention, switch S of FIG. 1 of that patent is omitted (i.e. consider switch S to be held open at all times). For brevity, magnetic field responsive circuitry for disabling detectors 510 and 520 has been omitted from the drawings but may comprise a desirable option.

Briefly considering the operation of components 104 and 108 – 111 in the illustrated pacer with switch 100 open as shown, current from the series string of batteries flows through resistor 59 and charges up capacitor 65 which holds the voltage as long as transistor T9 is not turned on. Current from the series string of batteries also flows through the parallel series circuit including the parallel combination of diode 104 and resistor 108, series resistor 109 and the parallel combination of capacitor 111 and resistor 110.

If the heart demands a stimulating impulse, transistors T7 and T8 cause transistor T9 to conduct, causing capacitor 65 to discharge through ventricular electrodes E2, E3, and the heart 6. The transistors T7 and T8 comprise a relaxation oscillator which is timed by the rate at which capacitor 57 charges (trace 270 in FIGS. 2-4) to the threshold voltage level appearing at the base of transistor T7 (junction J). When the voltage on capacitor 57 is such that the timing voltage 270 on the emitter of transistor T7 is equal to that on its base (junction J), the relaxation oscillator is triggered, causing transistor T9 to conduct. When transistors T7 and T8 conduct, capacitor 57 is discharged and thus reset. Transistor T6 is connected across timing capacitor 57 and is responsive to a pulse on conductor 580 from capacitor 53 each time an R-wave is detected for conducting and thereby also discharging and resetting capacitor 57. In this manner, detected R-waves act to reset the relaxation oscillator before completion of a basic interval (800 ms) or cycle in order to prevent a ventricular stimulation impulse from being generated during the vulnerable period following a ventricular contraction.

When T8 conducts, some of the current for the collector of T8 comes from the charged capacitor 111. After T8 stops conducting capacitor 111 recharges to its former state through resistors 108 and 109. Capacitor 111 is chosen so that it does not recharge to its previous static voltage value in a time equal to or less than the time between pulses in the ordinary heart rate to provide what is known in the prior art as rate hysteresis.

The P-wave detector 520 responds to each P-wave by generating a trigger pulse 561 which is applied to the triggering input of monostable 600 via conductor 560. The input to monostable 600 is connected to one side of a coupling capacitor 601 which is analogous to capacitor 53 in the R-wave detection circuitry of U.S. Pat. No. 3,528,428. While the trigger pulse 561 applied to monostable 600 is herein illustrated as being positive it will be appreciated that a pulse of opposite polarity might be provided if required.

Referring to FIG. 7, the monostable 600 comprising the automatic A-V interval control of the present invention is illustrated in greater detail. The general configuration of monostable multivibrator 600 may be any of several general types and is here shown as being of the collector-coupled transistor type in which a pair of NPN transistors T20 and T21 have their emitters connected in common to the same potential, here denoted as Vo and corresponding with an intermediate voltage from the battery-series B1-B5. As is well known, a monostable multivibrator has a stable state and a metastable state. In the illustrated embodiment, T20 is biased "off" or in non-conduction and T21 is "on" or in saturation in the stable state.

The respective collectors of transistors T20 and T21 are connected to a voltage V+ relatively more positive than V− at their emitters through resistors 604 and 605 respectively. The base of T21 is cross coupled to the collector of T20 through timing capacitor 606. The base of T20 is cross coupled to the collector of T21 through resistor 607. A biasing resistor 608 connected between the base of T20 and a voltage V- relatively more negative than Vo at its emitter serves, with resistor 607, to form a voltage divider for biasing T20 off. A timing resistor 610 connected to the junction of capacitor 606 and the base of T21 extends to the voltage also applied to resistors 604 and 605. Resistor 610 may be variable for selecting and presetting a nominal duration for A-V interval pulse 620. A pair of oppositely-poled steering diodes (not shown) biased by resistor 608 might extend from coupling capacitor 601 to the respective bases of T20 and T21 so that an incoming rigger pulse of either polarity might be used to switch monostable 600 from its stable state to the metastable state.

Figure 8:
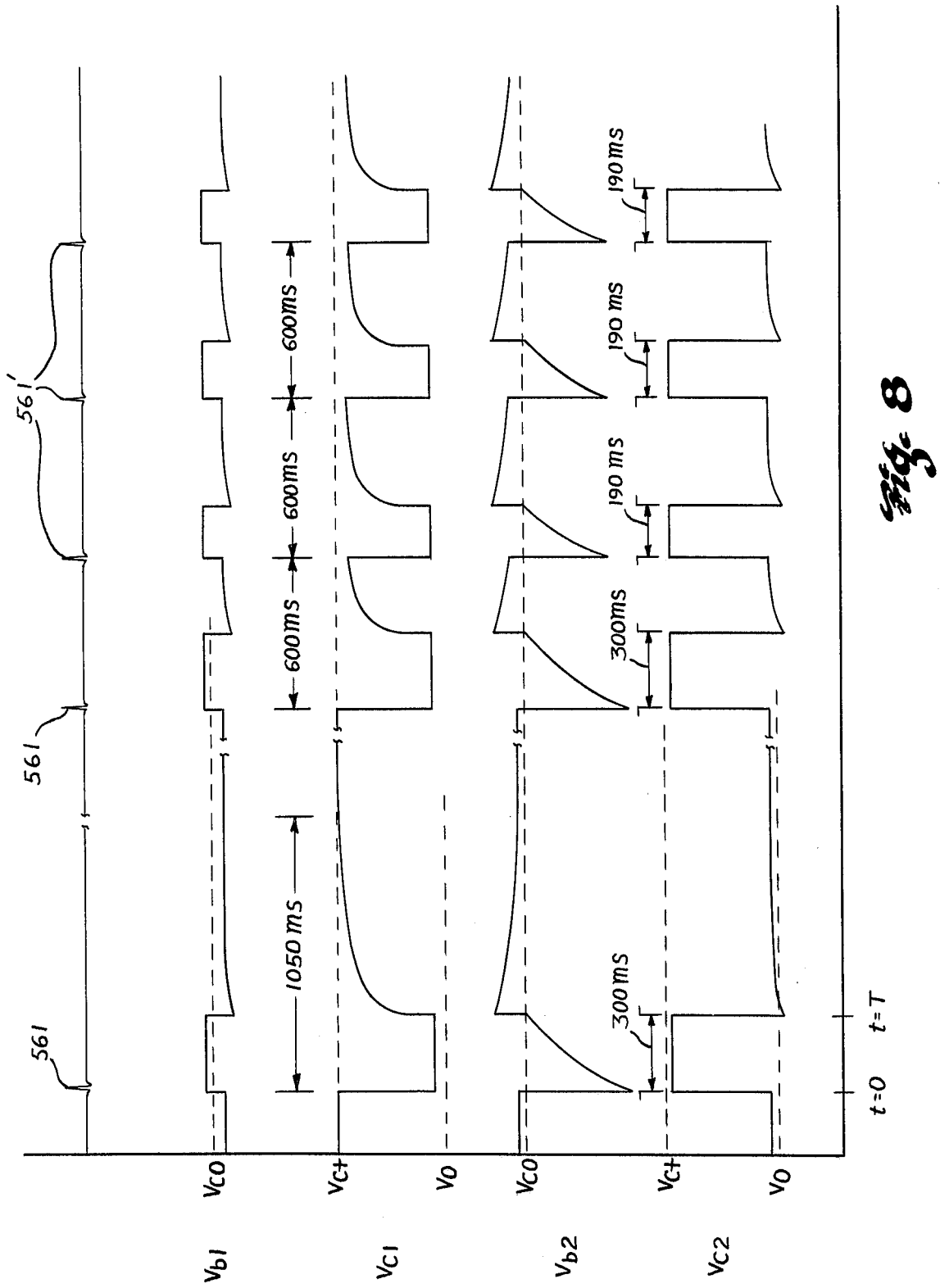
FIG. 8 is a graphical time plot of the voltage waveforms occurring at several significant locations in the A-V interval control monostable of FIG. 7.

Referring to FIG. 7 and the waveforms of FIG. 8, when a positive trigger pulse 561 is applied to the base of T20 at $t=0$, the high positive voltage $V_{c1}$ at the collector of T20 begins to fall (becomes less positive or more negative). This negative going voltage is coupled to the base of T21 and the forward bias is decreased. The base current and collector current of T21 begins to decrease. The collector voltage $V_{c2}$ of T21 increases positively. A portion of this voltage is coupled through resistor 607 to the base of T20, increasing its potential $V_{b1}$ positively. This regeneration results in a rapid change of both T20 and T21. Since capacitor 606 was initially charged to a potential almost equal to the voltage V+ appearing on the common terminals of resistors 604, 610 and 605, the base of T21 is now at a negative potential almost equal to the magnitude of the difference between Vo and V+.

Capacitor 606 discharges through resistor 610 and the low saturation resistance of T20. The base potential $V_{b2}$ of transistor T21 becomes less negative. Generally speaking, when the base potential of transistor T21 becomes slightly positive of the cut-off voltage $V_{co}$ at $t=T$, T21 again conducts; the collector potential of T21 increases negatively and is coupled to the base of T20 driving it into cut-off; and transistor T20 is again at cut-off and T21 is in saturation with its collector voltage almost at Vo. This stable condition is maintained until another pulse triggers the circuit. The A-V interval pulse ($V_{c2}$) is taken from the collector of T21 and its normal maximum duration as a relatively positive rectangular waveform is primarily determined by the RC time constant of resistor 610 and capacitor 606 during the above mentioned discharge of the capacitor. The magnitude of the A-V interval pulse may be variably preset by replacing resistor 605 with a potentiometer or series pair of resistors and deriving the pulse at the wiper or junction. The cut-off voltages $V_{co}$ for the bases of T20 and T21 is slightly below $V_o$.

The normal duration of A-V interval pulse 620 is represented by the interval from $t=0$ to $t=T$ in FIG. 8. This assumes, however, that the recovery timing circuit including resistor 604 and the capacitor 606 has had sufficient time to return the monostable 600 to a quiescent stable state before the next trigger pulse, according to the generally preferred mode of operation of monostables in various applications including prior art pacers. (See pages 184-185 and 600-602 of Pulse and Digital Circuits, by Millman and Taub, McGraw Hill, 1956).

However, in accordance with the present invention, the time constants of the A-V interval and of the recovery circuits of monostable 600 are selected to be of such duration that trigger pulses recurring at the rates associated with heart rates in the range of 55 - 140 beats per minute operate to reduce the duration of A-V interval pulse 620 from that normal or maximum duration obtained when successive trigger pulses occur at intervals greater than the sum of the normal maximum duration plus the recovery time. This reduction in the normal duration of the output pulses is, in other instances and applications, considered undesirable and is explained in greater detail at the aforementioned pages in Pulse and Digital Circuits.

Briefly, the voltage at the base of T21 rises exponentially toward V+ just after a trigger pulse and experiences an overshoot when T21 goes on and T20 goes off. Further, the capacitor 606 must recharge through resistor 604 in series also with the much smaller resistance $r$ of the emitter-base circuit of T21. In order that the normal maximum duration of the output pulse of monostable 600 not be disturbed, the overshoot on the base of T21 must fully decay and the capacitor 606 must fully recharge to place the collector of T20 to V+. Both these functions require the same time, the so called recovery time, which depends on the time constant $(R+r)C$, where R is the value of resistor 604, $r$ is the much smaller value of the emitter base resistance of T21, and C is the value of capacitor 606.

If a subsequent trigger pulse, designated 561¹ in FIG. 8, occurs before completion of the minimum recovery time, the subsequent change in voltage $V_{c1}$ at the collector of T20 is less than "normal". The main result is that the following sudden negative decrease in the voltage $V_{b2}$ at the base of T21 is correspondingly less than normal, such that capacitor 606 then begins to discharge through resistor 610 at a voltage relatively closer to V+ than normal, thereby shortening the interval during which T21 does not conduct to provide the A-V pulse 620 of less than normal maximum duration.

In the present embodiment, the values of resistor 610 and capacitor 606 are selected such that the normal maximum duration of A-V interval pulse 620 is at least about 225-250 milliseconds (i.e. 300 ms). Further, the values of resistor 604 and capacitor 606 should be selected to provide a relatively long recovery time. For example, the normal maximum A-V interval of at least 225-250 milliseconds may be selected to correspond with heart rates below about 58 beats per minute, and increases in the heart rate up to about 140 beats per minute should result in corresponding reductions in the duration of the A-V interval pulse to a limit of about 125 - 150 milliseconds.

It will be appreciated that the normal maximum duration of the output pulse (620) from monostable 600 could conceivably be as much as 700-900 milliseconds, but the values of resistors 604 and 610 and capacitor 606 should be such that for trigger rates (i.e. sensed P-wave or heart rates) of about 55-60 per minute the duration of the output pulse 620 would be shortened to about 225-250 ms with attendant further continuous shortening to about 125-150 ms for respective further heart rate increases to about 140 per minute.

Generally speaking, the reduction in the interval as a function of the increase in heart rate over the contemplated operating range generally bears the relationship of about 1:1 or 1: 1½, and an appropriately sloped section of the exponential recovery time constant curve should be selected for operation. By making the value of resistor 604 relatively large, the several hundred-ohm value of base-emitter resistance $r$ may essentially be omitted in determining the $(R+r)$ C recovery time constant.

It will be further appreciated that if the normal maximum interval of the output pulse of monostable 600 is relatively long (i.e. 500-1000 ms), a relatively short recovery time constant may suffice; whereas if the normal maximum interval of the monostable is relatively short (i.e. 250-300 ms) the recovery time constant will need to be at least as long as the remainder of the 1000 - 1025 ms interval which corresponds with a heart rate of 60 - 55 beats per minute.

It is preferable that triggering of monostable 600 be conducted in that portion of the recovery time constant curve having a relatively small slope in order to minimize the change in the A-V interval during alternate triggerings at any constant trigger rate as described at pages 185-186 of Pulse and Digital Circuits. This consideration suggests, then, that the normal maximum interval of the output pulse from monostable 600 be relatively near 250 ms to allow a long recovery time constant with subsequent triggering occuring during the "flatter" later portion thereof.

Figure 3:
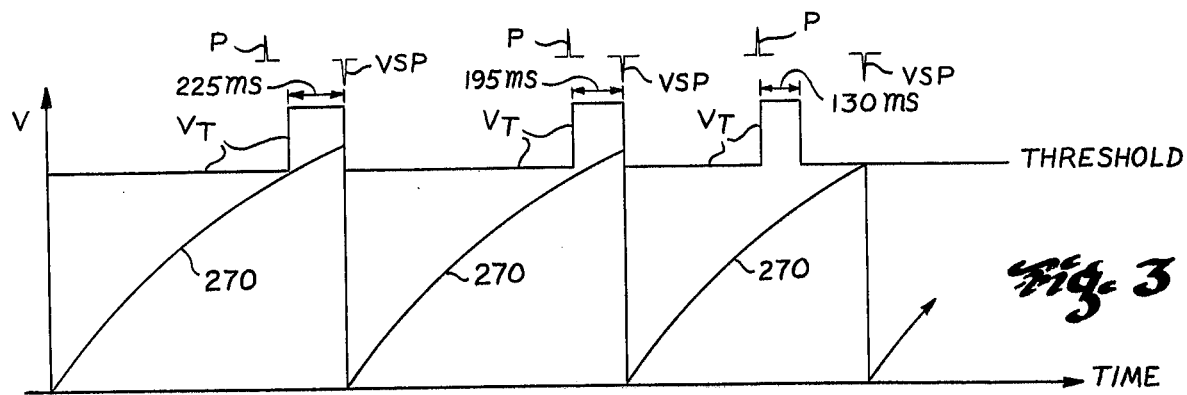
FIG. 3 comprises graphical representations similar to FIG. 2, though not necessarily in contiguous sequence, showing the threshold voltage modified in accordance with one aspect of the invention.

Having discussed the novel means by which the interval of A-V interval pulse 620 is varied as a function of sensed atrial heart rate, the resulting pulse 620 is then extended to the junction J at the base of T7 to adjust the theshold voltage $V_T$ thereat in accordance with the disclosure in the aforementioned application Ser. No. 726,887. If pulse 620 is connected directly to junction J (excluding or bypassing capacitor 630), the voltage $V_T$ is elevated by that of the pulse 620 throughout its duration such that the ventricular stimulation pulse (VSP) timing interval may be extended, as illustrated in FIG. 3, beyond the free running interval illustrated in FIG. 2. The ventricular pulse timing interval may be extended by as much as the interval of the A-V pulse 620, if the latter begins (as the result of P-wave, P) just before time-out of the basic 800 ms timing interval of the relaxation oscillator. In this somewhat restricted embodiment, ventricular stimulation pulses, VSP, may occur (assuming no inhibition by natural ventricular contractions) at intervals in the range between 800 ms and 800 ms plus the interval of A-V pulse 620. For instance, if it is desired to provide stimulation pulses VSP in response to P-waves sensed at a rate as low as 55-60 per minute (1025 - 1000 ms interval), the interval of pulse 620 at that rate would be about 210-225 ms. Should the P-waves be occurring at a rate of 70 per minute (858 ms interval), the monostable 600 is scaled such that the interval of pulse 620 at that rate is about 190–200 ms. It will be appreciated that this arrangment, although allowing "slow-down" of the pacer from a basic rate, is limited in range (75 to 60–55 beats per minute), and thus would not require monostable 600 to vary the interval of pulse 620 more than about 50 – 75 ms. The right-most portion of FIG. 3 illustrates the situation of an increased P-wave rate, and thus shortened A-V interval (130 ms), in which the adjustment to $V_T$ is unable to control the generation of pulse VSP.

In a preferred arrangement, the A-V interval pulse 620 is extended through capacitor 630 to the junction J at the base of T7. By coupling pulse 620 through capacitor 630, the threshold potential at junction J is rapidly increased by the magnitude of pulse 620 and then begins to decay or "droop" as the capacitor 630 begins to charge at a rate determined by the time constant of the circuit through the capacitor and thence through the several parallel paths comprised of serial resistors 108 and 109, resistor 110 and capacitor 111. The rate of droop is preset by appropriate selection of values of the aforementioned circuit components and particularly capacitor 630. For instance, the less the capacitance of capacitor 630, the greater its charging rate and thus, the greater the rate of droop. It will be realized that the actual magnitude (voltage) of droop is a function of the duration of A-V pulse 620, which value is variable according to the present invention. Further, the aforementioned capacitor 111 included for purposes of rate hysterisis might be omitted, with an appropriate rescaling of capacitor 630 and the impedance of its charging circuit to retain the desired "droop". Such rescaling of capacitor 630 and its charging circuit might also be controlled to retain a degree of rate hysterisis, if desired.

Through this introduction of "droop" to the adjusted threshold potential $V_T$ at junction J it is possible to not only extend the ventricular pulse interval beyond the basic 800 ms rate, but also to reduce the interval to less than 800 ms for atrial beat rates which exceed 75 per minute; and which may be as great as 140 – 150 per minute. This may be seen in FIG. 4 where in the first instance (waveform 4A), the atrial beat rate is about 55 – 60 per minute, the P-wave, P, occurs at about 790 – 795 ms into the ventricular timing interval and the A-V interval pulse is of about 225 ms duration in accordance with the atrial rate and where in the second instance (waveforms 4B), occurring during a period of exercise, the atrial beat rate is about 140 per minute, the P-wave, P, occurs at about 290 ms into the ventricular timing interval and the A-V interval pulse is of about 140 ms duration in accordance with the present atrial beat rate. The magnitude (voltage) and rate of the "droop" in the adjusted threshold potential $V_T$ must be sufficiently great that the sudden decrease in potential $V_T$ at the termination of the A-V pulse intersects the rising timing voltage 270 for atrial beat rates as great as 140–150 per minute, however, it must not be so great that, when the A-V pulse is of 225 ms duration at atrial rates of 55 beats per minute, it prematurely intersects the rising timing voltage 270 before completion of the A-V interval. The surest way to accomplish this and insure the range of required "droop" magnitudes is with an A-V pulse of relatively large magnitude. Further, the RC time-constant of the circuit through which capacitor 630 charges should be less than the RC time-constant of the circuit through which the timing capacitor 57 charges in order to avoid the situation in which the P-wave occurs particularly early in the escape interval and the adjusted threshold voltage does not intersect the timing voltage on its downstep at the completion of the 200 millisecond A-V interval but sometime thereafter when the relatively "slower" recovering threshold voltage is met by the more rapidly rising timing voltage 270.

Figure 4:
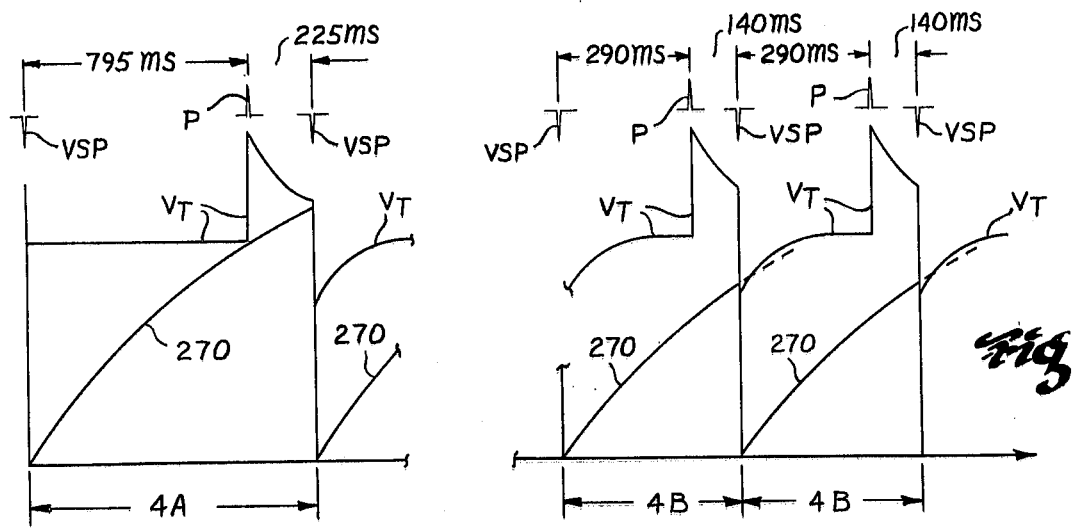
FIG. 4, waveforms 4A and 4B comprise graphical representations similar to FIG. 2, though not necessarily in contiguous sequence, showing the threshold voltage modified in accordance with another aspect of the invention.

Although not specifically illustrated in FIGS. 2–4, it will be appreciated that the occurrence of an R-wave is overriding and will inhibit the generation of a stimulation pulse by resetting the relaxation oscillator and thereby beginning anew the basic timing interval.

While preferred embodiments of the invention have been shown and described, various modifications and substitutions may be made thereto without departing from the spirit and scope of the present invention. Accordingly, it is to be understood that the present invention has been described by way of illustration and not limitation.

I claim:

1. In an atrial synchronous device for stimulating the heart of a patient, said device comprising terminal means for connection to said patient's heart, timing means for establishing timing intervals based on a basic interval, pulse generator means for generating a ventricular stimulation impulse on said terminal means at the end of each of said timing intervals to effect a beating action of the ventricle of said heart, first means for detecting the beating action of the atrium of said heart, means responsive to the operation of said first detecting means for generating an A-V interval pulse, said timing means including control means responsive to said A-V interval pulse for varying said timing interval relative to said basic interval within a predetermined range, the completion of a said varied timing interval coinciding with the completion of a respective said A-V interval pulse, and means responsive to at least said ventricular stimulation impulse for resetting said timing means, the improvement wherein said A-V interval pulse generating means comprises means responsive to successively detected beating actions of the atrium of said heart for automatically controlling the interval of the respectively generated A-V interval pulse as a function of the interval between said successively detected atrial beating actions.

2. The heart stimulating device of claim 1 wherein the interval between successive said atrial beating actions may vary and wherein the interval of a said A-V interval pulse varies in the same time-sense direction as a said variation in the respective interval between the immediately preceding detected atrial beating actions.

3. The heart stimulating device of claim 2 wherein said A-V interval pulse generating means comprises a monostable multivibrator, said multivibrator having first R-C timing means for determining the normal maximum duration of said A-V interval pulse and second R-C timing means for determining the minimum time for full recovery between successive said A-V interval pulses of maximum duration, said monostable multivibrator being triggered by each detected atrial beating action, a said A-V interval pulse being of less than said maximum duration if the respective triggering of said multivibrator occurs sooner than completion of said full recovery following termination of the preceding said A-V interval pulse, and said first and said second R-C timing means being preselected to provide a said A-V interval pulse of first duration when the interval between successive atrial beating actions is of one value and of second duration whorter than said first duration when the interval between successive atrial beating actions is of an other value shorter than said first value.

4. The heart stimulating device of claim 3 wherein said one value of the interval between successive atrial beating actions corresponds with a low-limit heart rate and said other interval value corresponds with a high-limit heart rate.

5. The heart stimulating device of claim 4 wherein said variation in the interval of said A-V interval pulse in the heart-rate range between said low-limit and said high-limit is substantially continuous across said range.

6. The heart stimulating device of claim 3 wherein said means for resetting said timing means includes second means for detecting the beating action of the ventricle of said heart and means responsive to said second detecting means for resetting said timing means.

7. The heart stimulating device of claim 3 wherein said control means for varying said timing interval comprises means for lengthening said timing interval beyond said basic interval if the otherwise next generated one of said ventricular stimulation impulses would have occurred during the time of occurrence of said A-V interval pulse and for limiting said lengthened intervals to be no longer than the sum of said basic interval and the interval of said A-V interval pulse and alternatively, for shortening said timing interval to less than said basic interval if said detected beating action of the atrium occurs within a predetermined interval ending prior to the end of said basic interval by said length of said A-V interval pulse.

* * * * *